US009704898B2

(12) United States Patent
Chung et al.

(10) Patent No.: US 9,704,898 B2
(45) Date of Patent: Jul. 11, 2017

(54) INTEGRATED BIO-SENSOR WITH NANOCAVITY AND FABRICATION METHOD THEREOF

(71) Applicant: Powerchip Technology Corporation, Hsinchu (TW)

(72) Inventors: Tse-Wei Chung, Taichung (TW); Tsung-Hui Chou, New Taipei (TW); Che-Hung Lin, Hsinchu (TW); Shao-Wei Lu, Hsinchu (TW); Hsiao-Pei Lin, Hsinchu (TW)

(73) Assignee: Powerchip Technology Corporation, Hsinchu (TW)

( * ) Notice: Subject to any disclaimer, the term of this patent is extended or adjusted under 35 U.S.C. 154(b) by 1 day.

(21) Appl. No.: 14/987,777

(22) Filed: Jan. 5, 2016

(65) Prior Publication Data

US 2017/0016830 A1 Jan. 19, 2017

(30) Foreign Application Priority Data

Jul. 15, 2015 (TW) .............................. 104122847 A (51) Int. Cl.
*H01L 27/146* (2006.01)
*H01L 31/0216* (2014.01)
*G01N 21/64* (2006.01)

(52) U.S. Cl.
CPC ... *H01L 27/14609* (2013.01); *G01N 21/6454* (2013.01); *H01L 27/14612* (2013.01); *H01L 27/14621* (2013.01); *H01L 27/14643* (2013.01); *H01L 27/14645* (2013.01); *H01L 27/14647* (2013.01); *H01L 31/02162* (2013.01); *G01N 2021/6482* (2013.01)

(58) Field of Classification Search
CPC ......... H01L 27/14605; H01L 27/14623; H01L 27/14609; H01L 27/14645; H01L 27/14612; H01L 27/14643; H01L 27/14647; H01L 31/02162
See application file for complete search history.

(56) References Cited

U.S. PATENT DOCUMENTS

| | | | | |
|---|---|---|---|---|
| 9,129,875 B2 * | 9/2015 | Yano | ................ | H01L 27/14621 |
| 9,224,777 B2 * | 12/2015 | Sawayama | ........ | H01L 27/14629 |
| 2006/0049439 A1 * | 3/2006 | Oh | .................... | H01L 27/14625 257/292 |
| 2011/0006387 A1 * | 1/2011 | Katsuno | ............ | H01L 27/14625 257/433 |
| 2012/0156100 A1 | 6/2012 | Tsai | | |
| 2016/0372507 A1 * | 12/2016 | Yang | ................ | H01L 27/14621 |

* cited by examiner

*Primary Examiner* — Jose R Diaz
(74) *Attorney, Agent, or Firm* — Winston Hsu (57) ABSTRACT

A bio-sensor includes a substrate having a light-sensing region thereon. A first dielectric layer, a diffusion barrier layer, and a second dielectric layer are disposed on the substrate. A trenched recess structure is formed in the second dielectric layer, which is filled with a light filter layer that is capped with a cap layer. A first passivation layer and a nanocavity construction layer are disposed on the cap layer. A nanocavity is formed in the nanocavity construction layer. The sidewall and bottom surface of the nanocavity is lined with a second passivation layer.

28 Claims, 10 Drawing Sheets

INTEGRATED BIO-SENSOR WITH NANOCAVITY AND FABRICATION METHOD THEREOF

BACKGROUND OF THE INVENTION

1. Field of the Invention

The invention relates to a bio-technology inspection field, and more particularly, to a bio-sensor with nanocavity and a fabrication method thereof.

2. Description of the Prior Art

In recent years, various biological inspection methods have been developed as a result of the progress in biotechnology, in which technologies involving the inspection of deoxyribonucleic acid (DNA) sequence within a specific gene have become especially popular. A gene is typically known as a particular sequence of DNA with deoxyribose and phosphates serving as backbone while having four bases including adenine (A), guanine (G), thymine (T), and cytosine (C). The matching of chemical structures between two single strands of DNA is preferably enhanced by the mutual attraction of hydrogen bonds between adenine and thymine, and between guanine and cytosine to constitute the double helix structure of a DNA.

It has been known that DNA sequencing could be achieved by slicing gene sequences waiting to be sequenced into small chunks, connecting the sliced chunks to a converting adaptor, selectively adding micro-beads with polymerase chain reaction (PCR) to multiply gene chucks waiting to be inspected, and finally combining micro-processes, optical inspections, and automated control technologies based on different sequencing principles to quickly decode large quantities of DNA sequence.

In addition to DNA sequencing, bio-sensors could also be applied to numerous bio-related inspections, such as bacterial and viral inspections, gene mutations, genetic or hereditary screenings, disease preventions, environmental inspections, pollution controls, and food safety. Moreover, bio-sensors could be applied to fast checks for genetic defects. Based on inspection data obtained, the bio-sensors could be used to provide currently unknown solutions for such as nucleic acid polymorphism differentiation and the relations between diseases and complications. The results thereby may further be used to develop diagnosing and preventing approaches.

However, there is still a need in this field to provide an improved bio-sensor capable of not only having advantages such as fast, high accuracy, and high sensitivity, but also having acid and alkali-resistant and anti-corrosive structures. The fabrication method of the improved bio-sensor should also be compatible with CMOS image sensors so that the signal processing circuit chips could be integrated for the purposes of cost reduction, power consumption reduction, and integrity enhancement.

SUMMARY OF THE INVENTION

To achieve the purposes described above, an integrated bio-sensor with a nanocavity and a fabrication method thereof are provided in the present invention for solving the inadequate parts and the demerits of the prior art.

An integrated bio-sensor with a nanocavity is provided in an embodiment of the present invention. The integrated bio-sensor includes a substrate, a light-sensing region, a first dielectric layer, a diffusion barrier layer, a second dielectric layer, a trenched recess structure, a liner layer, a light filter layer, a cap layer, a first passivation layer, a nanocavity construction layer, and a second passivation layer. A plurality of isolation structures are disposed on the substrate, and a plurality of pixel regions are defined by the isolation structures. The light-sensing region is disposed in each of the pixel regions. The first dielectric layer is disposed on the substrate. The diffusion barrier layer is disposed on the first dielectric layer. The second dielectric layer is disposed on the diffusion barrier layer. The trenched recess structure is disposed in the second dielectric layer. The liner layer is disposed conformally on an inner wall of the trenched recess structure. The light filter layer is disposed on the liner layer in the trenched recess structure. The cap layer directly contacts a top surface of the light filter layer, and the light filter layer is capped with the cap layer. The first passivation layer is disposed on the cap layer. The nanocavity construction layer is disposed on the first passivation layer. A nanocavity is disposed in the nanocavity construction layer disposed directly above the light filer layer. The second passivation layer is disposed on a sidewall and a bottom surface of the nanocavity. The light filter layer is configured to block light within a specific wavelength range and filter out noise light, and light within another specific wavelength range may pass through the light filter layer and irradiate the light-sensing region.

A fabrication method of an integrated bio-sensor with a nanocavity is provided in an embodiment of the present invention. The fabrication method includes the following steps. A substrate is provided. A plurality of isolation structures are disposed on the substrate, and a plurality of pixel regions are defined by the isolation structures. A light-sensing region is formed in each of the pixel regions. A first dielectric layer is deposited on the substrate. A diffusion barrier layer is deposited on the first dielectric layer. A second dielectric layer is deposited on the diffusion barrier layer. A trenched recess structure is formed in the second dielectric layer. A liner layer is deposited conformally on an inner wall of the trenched recess structure. A light filter layer is formed on the liner layer. The trenched recess structure is filled with the light filter layer. A cap layer is deposited to directly contact a top surface of the light filter layer, and the light filter layer is capped with the cap layer. A first passivation layer is formed on the cap layer. A nanocavity construction layer is deposited on the first passivation layer. A nanocavity is formed in the nanocavity construction layer directly above the light filer layer. A second passivation layer is formed on a sidewall and a bottom surface of the nanocavity.

According to an embodiment of the present invention, after the step of forming the light filter layer, the fabrication method further includes performing a solidification process for solidifying the light filter layer, and performing a polishing process or an etching back process for removing the light filter layer outside the trenched recess structure.

According to an embodiment of the present invention, the first passivation layer and the second passivation layer are formed by physical vapor deposition processes.

An integrated bio-sensor with a nanocavity is provided in another embodiment of the present invention. The integrated bio-sensor includes a substrate, a light-sensing region, a first dielectric layer, a diffusion barrier layer, a second dielectric layer, a trenched recess structure, a liner layer, a light filter layer, a cap layer, and a passivation layer. A plurality of isolation structures are disposed on the substrate, and a plurality of pixel regions are defined by the isolation structures. A light-sensing region is disposed in each of the pixel regions. The first dielectric layer is disposed on the substrate. The diffusion barrier layer is disposed on the first dielectric layer. The second dielectric layer is disposed on the diffusion barrier layer. The trenched recess structure is disposed in the second dielectric layer. The liner layer is disposed conformally on an inner wall of the trenched recess structure. The light filter layer is disposed on the liner layer in the trenched recess structure. The light filter layer has a top surface, and the top surface of the light filter layer is lower than a top surface of the first dielectric layer by a predetermined depth for forming a recess part. The cap layer is disposed conformally on the trenched recess structure. The cap layer directly contacts the top surface of the light filter layer; and the light filter layer is capped with the cap layer. The passivation layer is disposed conformally on the cap layer, wherein a surface of the passivation layer is self-aligned with the light filter layer for forming a nanocavity above the recess part.

A fabrication method of an integrated bio-sensor with a nanocavity is provided in another embodiment of the present invention. The fabrication method includes the following steps. A substrate is provided. A plurality of isolation structures are disposed on the substrate, and a plurality of pixel regions are defined by the isolation structures. A light-sensing region is formed in each of the pixel regions. A first dielectric layer is deposited on the substrate. A diffusion barrier layer is deposited on the first dielectric layer. A second dielectric layer is deposited on the diffusion barrier layer. A trenched recess structure is formed in the second dielectric layer. A liner layer is deposited conformally on an inner wall of the trenched recess structure. A light filter layer is formed on the liner layer. The trenched recess structure is filled with the light filter layer. A solidification process is performed for solidifying the light filter layer, and a polishing process or an etching back process is performed for removing the light filter layer outside the trenched recess structure. An etching back process is performed to make a top surface of the light filter lower than a top surface of the first dielectric layer by a predetermined depth for forming a recess part. A cap layer is deposited conformally on the recess part. The cap layer directly contacts the top surface of the light filter layer, and the light filter layer is capped with the cap layer. A passivation layer is formed conformally on the cap layer, wherein a surface of the passivation layer is self-aligned with the light filter layer for forming a nanocavity above the recess part. The passivation layer includes metal oxide, such as tantalum oxide.

These and other objectives of the present invention will no doubt become obvious to those of ordinary skill in the art after reading the following detailed description of the preferred embodiment that is illustrated in the various figures and drawings.

BRIEF DESCRIPTION OF THE DRAWINGS

The accompanying drawings are included to provide a further understanding of the embodiments, and are incorporated in and constitute apart of this specification. The drawings illustrate some of the embodiments and, together with the description, serve to explain their principles. In the drawings.

It is noted that all of the drawings in this specification are schematic drawings. For clearly and conveniently illustration, the size of each part and the scale between the parts in the drawings might be exaggerated or shrunk. Generally, characteristic components and the corresponding modified components will be marked by the same reference symbol, or the corresponding or similar components in different embodiments will be marked by the same reference symbol.

DETAILED DESCRIPTION

In the following detailed description of the invention, reference is made to the accompanying drawings, which form a part hereof, and in which is shown, by way of illustration, specific embodiments in which the invention may be practiced. These embodiments are described in sufficient detail to enable those skilled in the art to practice the invention. Other embodiments may be utilized and structural changes may be made without departing from the scope of the present invention.

The following detailed description is, therefore, not to be taken in a limiting sense, and the scope of the present invention is defined only by the appended claims, along with the full scope of equivalents to which such claims are entitled. One or more implementations of the present invention will now be described with reference to the attached drawings, wherein like reference numerals are used to refer to like elements throughout, and wherein the illustrated structures are not necessarily drawn to scale.

The term substrate is used to refer to and include a base material or a structure for forming components such as semiconductor units thereon. The substrate may be a semiconductor substrate, a semiconductor base material formed on a supporting structure, or a semiconductor substrate with one or more materials, structures, or regions formed thereon. The substrate may be a traditional silicon substrate or a bulk material containing semiconductor material. Apart from the traditional silicon wafer, the term substrate may also include a silicon-on-insulator (SOI) substrate, such as a silicon-on-sapphire (SOS) substrate, a silicon-on-glass (SOG) substrate, and a silicon epitaxial layer on a silicon base material, or other semiconductor or photoelectric materials, such as silicon germanium (SiGe), germanium (Ge), gallium arsenide (GaAs), gallium nitride (GaN), and indium phosphide (InP).

In this specification, when some component is described to be located on or above another component, it is referred to the conditions that the component is directly located right above the other component, the component is directly located adjacent to the other component, the component is directly located under the other component, or the component directly contacts the other component. The conditions that the component is indirectly located right above the other component, the component is indirectly located adjacent to the other component, the component is indirectly located under the other component, or the component does not directly contact the other component are also included in the description mentioned above. On the contrary, when some component is described to be directly located on another component, there is not any other component between this two components.

Unless there is a description mentioned specifically in the specification, the materials described in the specification may be formed by any appropriate technology, such as spin coating, slit coating, immersion coating, blanket coating, chemical vapor deposition (CVD), atomic layer deposition (ALD), and physical vapor deposition (PVD), but not limited thereto. Otherwise, the materials may be formed in-situ. One of ordinary skill in the art may select the appropriate technology to deposit or form the materials according to the properties of the specific materials to be formed.

Unless there is a description mentioned specifically in the specification, the actions of removing the materials in the specification may be achieved by any appropriate technology, such as etching process or polishing process, but not limited thereto.

An integrated bio-sensor is provided in the present invention, and a nanocavity capable of performing biochemical reactions directly is formed on the integrated bio-sensor. The integrated bio-sensor has advantages such as fast, high accuracy, and high sensitivity, and has an acid and alkali resisting and an anti-corrosion structure. The manufacturing process of the bio-sensor may be compatible with the manufacturing process of CMOS image sensor (CIS), the signal processing circuit chip may be integrated, and the purposes of cost reduction, power consumption reduction, and integrity enhancement may be achieved accordingly.

Figure 1:
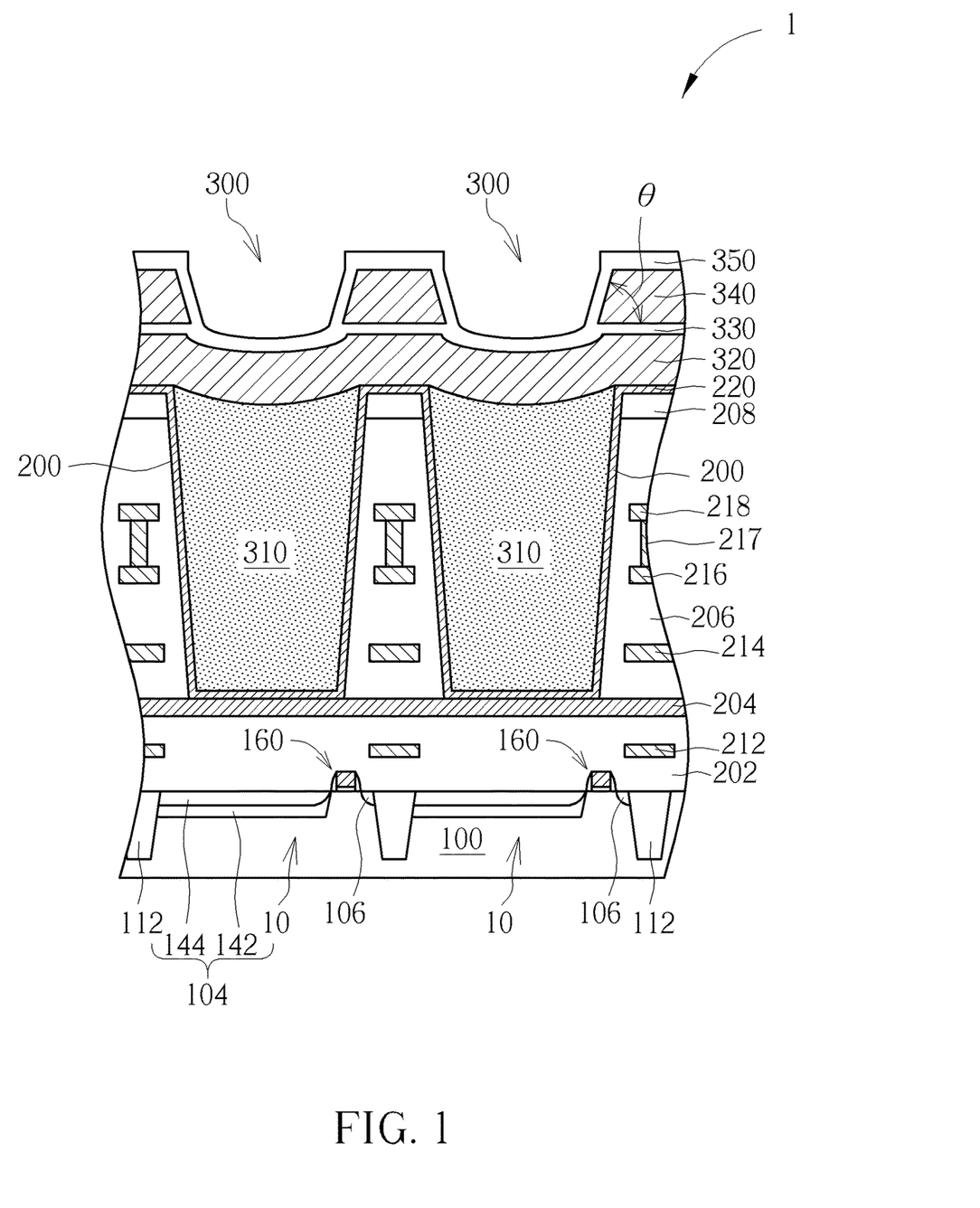
FIG. 1 is a schematic drawing illustrating a cross-sectional view of a bio-sensor with a nanocavity according to an embodiment of the present invention.

Please refer to FIG. 1. FIG. 1 is a schematic drawing illustrating a cross-sectional view of a bio-sensor with a nanocavity according to an embodiment of the present invention. As shown in FIG. 1, an integrated bio-sensor 1 includes a substrate 100, and a plurality of pixel regions 10 arranged in an array configuration are formed in the substrate 100. For describing conveniently, there are only two pixel regions of the pixel array shown in the figure. According to the embodiment the present invention, the substrate 100 may be a silicon substrate, but not limited thereto. A plurality of isolation structures 112 are disposed on the substrate 100, and a plurality of the pixel regions 10 are defined by the isolation structures 112.

A gate structure 160 may be formed on the substrate 100 of each pixel region. A light-sensing region 104 and a floating drain region 106 are then formed in the substrate 100 at two sides of the gate structure 160. The gate structure 160 may include a dielectric layer and a conductive layer. The dielectric layer may be silicon oxide, and the conductive layer may be single-crystal silicon, undoped polycrystalline silicon, doped polycrystalline silicon, amorphous silicon, metal silicide, or the combination of the materials mentioned above. A sidewall spacer may be formed on the sidewall of the gate structure 160, and the sidewall spacer may be silicon oxide, silicon nitride, or the combination of silicon oxide and silicon nitride.

The light-sensing region 104 may be a photodiode including a first conductivity type doped region 142 and a second conductivity type doped region 144. The first conductivity type is an opposite conductivity type of the second conductivity type. For example, when the substrate is a P type substrate, the first conductivity type doped region 142 may be an N type doped region, the second conductivity type doped region 144 may be a P type doped region, the floating drain region 106 may be an N type doped region, and vice versa. For instance, the first conductivity type doped region 142 may be a lightly doped region, and the second conductivity type doped region 144 and the floating drain region 106 may be heavily doped regions.

According to the embodiment of the present invention, multiple dielectric layers, such as a dielectric layer 202, a dielectric layer 204, a dielectric layer 206, and a dielectric layer 208, may be formed on the substrate 100. For example, the dielectric layer 202 and the dielectric layer 206 may include silicon dioxide, but not limited thereto. The dielectric layer 204 disposed between the dielectric layer 202 and the dielectric layer 206 may include silicon nitride, but not limited thereto. According to the embodiment of the present invention, the dielectric layer 204 is used as a diffusion barrier layer. The dielectric layer 208 is used as a passivation layer or a protection layer, and the dielectric layer 208 may include silicon nitride, silicon oxynitride, and/or silicon oxide, but not limited thereto. According to the embodiment of the present invention, a metal layer 212 may be formed in the dielectric layer 202. A metal layer 214, a metal layer 216, a metal layer 218, and a metal connection 217 may be formed in the dielectric layer 206. It is noted that the metal layer structure in the dielectric layer shown in the figures is only used as an illustration sample. In other embodiments of the present invention, there may be more metal layers formed in the dielectric layers.

According to the embodiment of the present invention, a trenched recess structure 200 is formed in the dielectric layer 206 and the dielectric layer 208 above the light-sensing region 104 corresponding to each pixel region 10. According to the embodiment of the present invention, a bottom part of the trenched recess structure 200 is a top surface of the dielectric layer 204. In other words, a depth of the trenched recess structure 200 is substantially equal to a total thickness of the dielectric layer 206 and the dielectric layer 208. According to the embodiment of the present invention, a liner layer 220, such as silicon nitride layer, is formed conformally on the bottom part and an inner wall of the trenched recess structure 200, but not limited thereto. According to the embodiment of the present invention, the liner layer 220 may be further formed on a top surface of the dielectric layer 208 for forming a continuous liner layer.

According to the embodiment of the present invention, the trenched recess structure 200 may be filled with at least one light filter layer 310. According to the embodiment of the present invention, the light filter layer 310 is capable of blocking light within a specific wavelength range (such as a green light laser) and filtering out noise light, and light within another specific wavelength range (such as a fluorescence generated by a specific biochemical reaction) may pass through the light filter layer 310 and irradiate the pixel region 10 below. Corresponding electrical current signals may be generated by the photoelectric reaction in the pixel region 10 and then be received by the light-sensing region 104.

According to the embodiment of the present invention, the light filter layer 310 may include high concentration metal ions, such as sodium ions ($Na^+$). In the present invention, in order to prevent the metal ions from diffusing outward to the dielectric layer and inducing corrosion or deterioration of the metal layer, the surroundings and the bottom part of the light filter layer 310 are covered by the liner layer 220 for preventing the adjacent dielectric layer from directly contacting the light filter layer 310. Additionally, the dielectric layer 204 may be used as a diffusion barrier layer configured to keep the light filter layer 310 from diffusing downward to the surface of the substrate 100 and affecting the characteristics and performance of the devices.

According to the embodiment of the present invention, a cap layer 320 is stacked on the light filter layer 310 and the liner layer 220, and the cap layer 320 may be a silicon nitride layer for example, but not limited thereto. According to the embodiment of the present invention, the cap layer 320 directly contacts the top surface of the light filter layer 310, and the light filter layer 310 is capped with the cap layer 320. According to the embodiment of the present invention, the cap layer 320, the liner layer 220 and the dielectric layer 204 may be used to completely block the metal ions in the light filter layer 310 from diffusing outward.

According to the embodiment of the present invention, a first passivation layer 330 is formed on the cap layer 320. The first passivation layer 330 may be metal oxide, such as tantalum oxide (TaO), but not limited thereto. According to the embodiment of the present invention, the first passivation layer 330 has to be transparent, acid resistant, and alkali-resistant. The first passivation layer 330 has high etching selectivity in comparison with a nanocavity construction layer 340, such as a silicon nitride layer. According to the embodiment of the present invention, the first passivation layer may be used as an etching stop layer. According to the embodiment of the present invention, the first passivation layer 330 may be formed by a physical vapor deposition (PVD) process, but not limited thereto.

According to the embodiment of the present invention, a nanocavity construction layer 340, such as a silicon nitride layer, is formed on the first passivation layer 330, but not limited thereto. A nanocavity 300 is formed in the nanocavity construction layer 340 directly above the light filer layer 310. A depth of the nanocavity 300 is substantially equal to a thickness of the nanocavity construction layer 340. The sidewall of the nanocavity 300 is a bevel sidewall, and an included angle θ between the sidewall and a horizontal level may range between 60 degrees and 80 degrees, but not limited thereto.

According to the embodiment of the present invention, a second passivation layer 350 is conformally formed on the nanocavity construction layer 340, the sidewall of the nanocavity 300, and a bottom surface of the nanocavity 300. The second passivation layer 350 may be metal oxide, such as tantalum oxide (TaO), but not limited thereto. According to the embodiment of the present invention, the second passivation layer 350 has to be transparent, acid resistant, and alkali-resistant so as to prevent from the corrosion of biochemical reactions. According to the embodiment of the present invention, the second passivation layer 350 may be formed by a physical vapor deposition (PVD) process, but not limited thereto. The nanocavity 300 mentioned above has the bevel sidewall, and the step coverage of depositing the second passivation layer 350 may be better accordingly.

According to the embodiment of the present invention, for example, a reference sample may be disposed in the nanocavity, and a target sample may then be injected in each nanocavity 300. After a radiation by a specific laser light source, biochemical reactions are caused by the reference sample and the target sample for generating a fluorescence having a wavelength in a specific range. The specific wavelength fluorescence mentioned above may pass through the light filter layer 310 and irradiate the light-sensing region 104 for being sensed. The laser beam of the laser light source mentioned above will be filtered out by the light filter layer 310.

Figure 2:
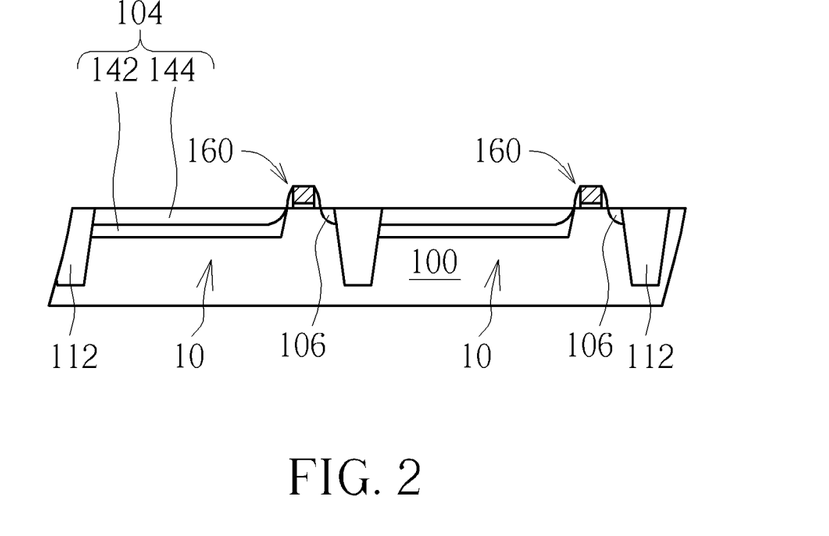
FIGS. 2-6 are schematic drawings illustrating a fabrication method of the bio-sensor with the nanocavity in FIG. 1.

Please refer to FIGS. 2-6. FIGS. 2-6 are schematic drawings illustrating a fabrication method of the bio-sensor with the nanocavity in FIG. 1. As shown in FIG. 2, a substrate 100 is provided first. A plurality of pixel regions 10 arranged in an array configuration are formed in the substrate 100. For describing conveniently, there are only two pixel regions of the pixel array shown in the figures. According to the embodiment the present invention, the substrate 100 may be a silicon substrate, but not limited thereto. A plurality of isolation structures 112 are disposed on the substrate 100, and a plurality of the pixel regions 10 are defined by the isolation structures 112.

A gate structure 160 may be formed on the substrate 100 of each pixel region. A light-sensing region 104 and a floating drain region 106 are then formed in the substrate 100 at two sides of the gate structure 160. The gate structure 160 may include a dielectric layer and a conductive layer. The dielectric layer may be silicon oxide, and the conductive layer may be single-crystal silicon, undoped polycrystalline silicon, doped polycrystalline silicon, amorphous silicon, metal silicide, or the combination of the materials mentioned above. A sidewall spacer may be formed on the sidewall of the gate structure 160, and the sidewall spacer may be silicon oxide, silicon nitride, or the combination of silicon oxide and silicon nitride.

The light-sensing region 104 may be a photodiode including a first conductivity type doped region 142 and a second conductivity type doped region 144. The first conductivity type is an opposite conductivity type of the second conductivity type. For example, when the substrate is a P type substrate, the first conductivity type doped region 142 may be an N type doped region, the second conductivity type doped region 144 may be a P type doped region, the floating drain region 106 may be an N type doped region, and vice versa. For instance, the first conductivity type doped region 142 may be a lightly doped region, and the second conductivity type doped region 144 and the floating drain region 106 may be heavily doped regions.

Figure 3:
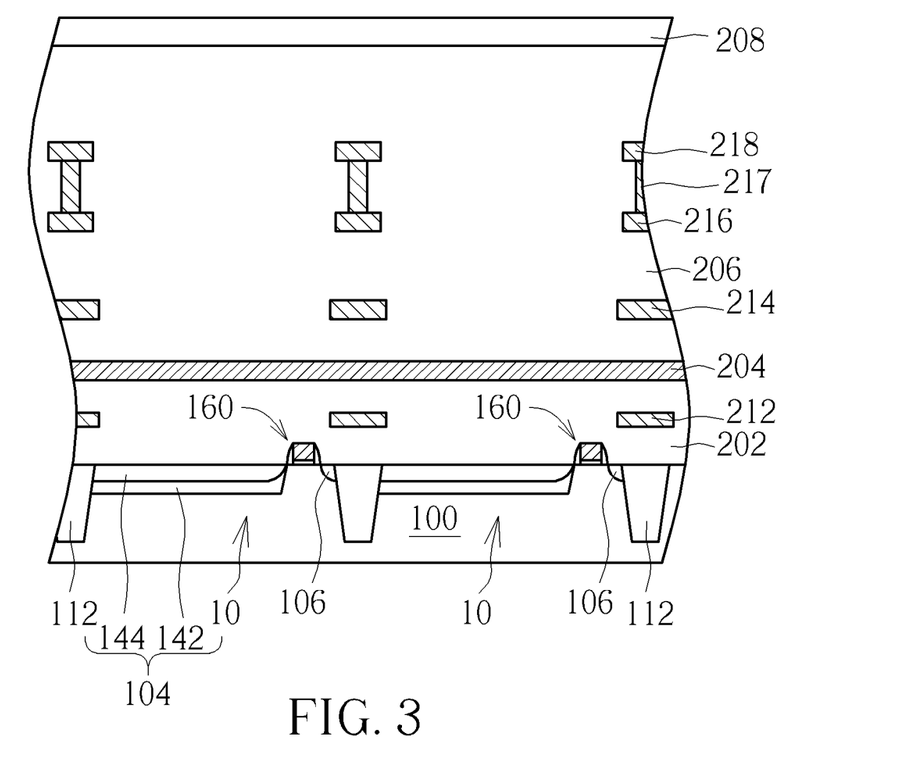

As shown in FIG. 3, multiple dielectric layers including a dielectric layer 202, a dielectric layer 204, a dielectric layer 206, and a dielectric layer 208, a metal layer 212, a metal layer 214, a metal layer 216, and a metal layer 218 are deposited on the substrate 100. For example, the dielectric layer 202 and the dielectric layer 206 may include silicon dioxide, but not limited thereto. The dielectric layer 202 and the dielectric layer 206 may be composed of multiple dielectric layers. The dielectric layer 204 formed between the dielectric layer 202 and the dielectric layer 206 may include silicon nitride, but not limited thereto. According to the embodiment of the present invention, the dielectric layer 204 is used as a diffusion barrier layer. The dielectric layer 208 is used as a passivation layer or a protection layer, and the dielectric layer 208 may include silicon nitride, silicon oxynitride, and/or silicon oxide, but not limited thereto. According to the embodiment of the present invention, the metal layer 212 may be formed in the dielectric layer 202. The metal layer 214, the metal layer 216, the metal layer 218, and the metal connection 217 may be formed in the dielectric layer 206. It is noted that the metal layer structure in the dielectric layer shown in the figures is only used as an illustration sample. In other embodiments of the present invention, there may be more metal layers formed in the dielectric layers.

Figure 4:
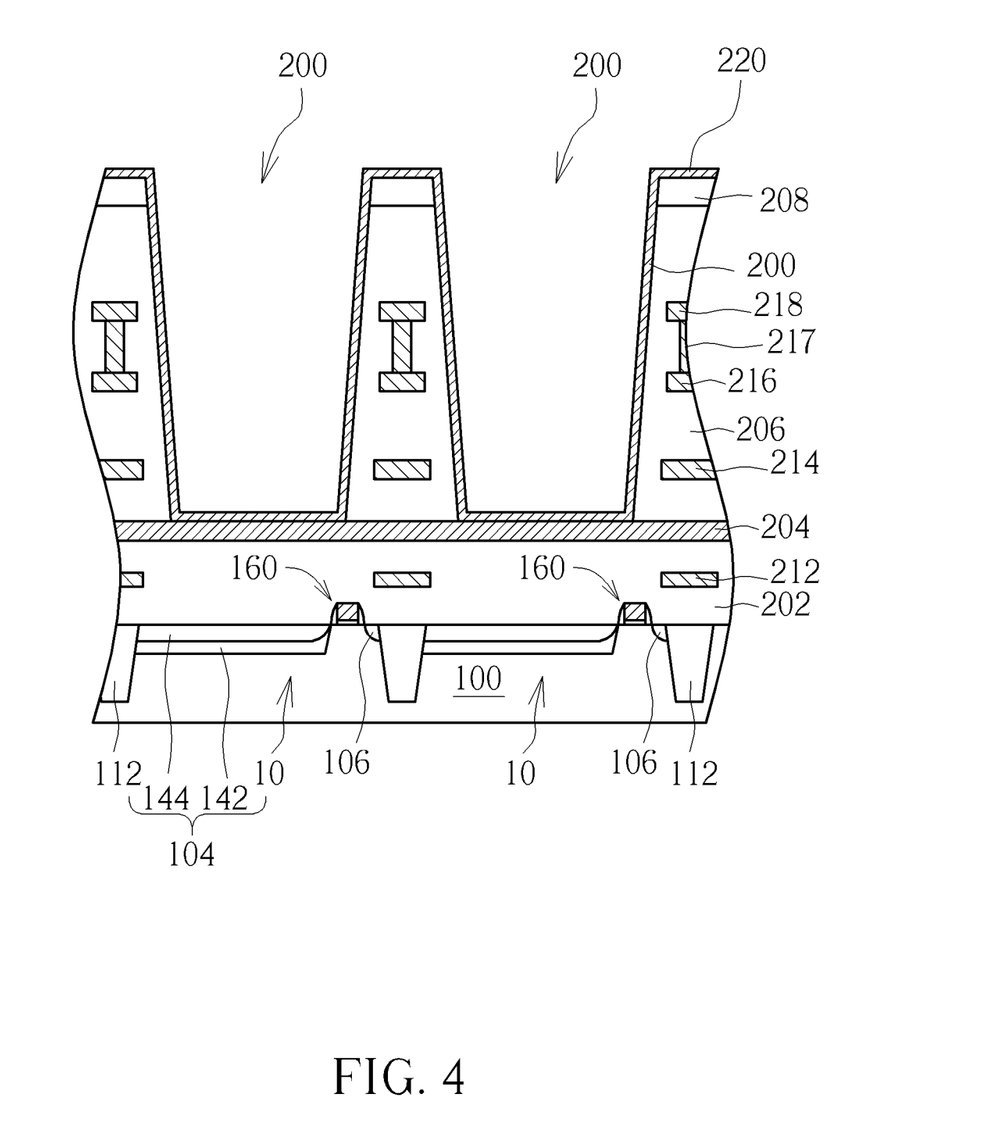

As shown in FIG. 4, a photolithographic process and an etching process are then performed to form a trenched recess structure 200 in the dielectric layer 206 and the dielectric layer 208 above the light-sensing region 104 corresponding to each pixel region 10. In the above-mentioned etching process for forming the trenched recess structure 200, the dielectric layer 204 may be used as an etching stop layer. According to the embodiment of the present invention, a bottom part of the trenched recess structure 200 is a top surface of the dielectric layer 204. In other words, a depth of the trenched recess structure 200 is substantially equal to a total thickness of the dielectric layer 206 and the dielectric layer 208. A liner layer 220, such as silicon nitride layer, is then deposited conformally on the bottom part and an inner wall of the trenched recess structure 200, but not limited thereto. According to the embodiment of the present invention, the liner layer 220 may be further formed on a top surface of the dielectric layer 208 for forming a continuous liner layer.

Figure 5:
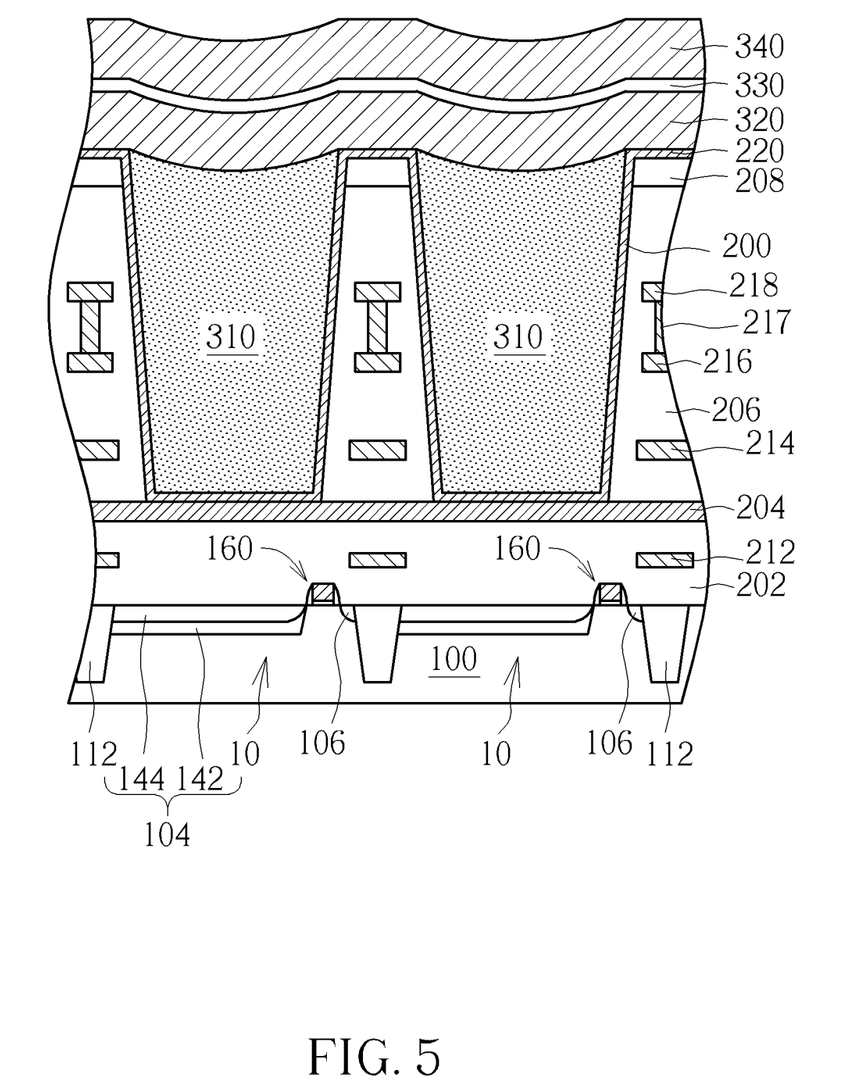

As shown in FIG. 5, the trenched recess structure 200 may then be filled with at least one light filter layer 310. According to the embodiment of the present invention, after the step of forming the light filter layer 310, a solidification process may then be performed for solidifying the light filter layer 310. According to the embodiment of the present invention, a polishing process or an etching back process may then be performed for removing the light filter layer 310 outside the trenched recess structure 200. According to the embodiment of the present invention, the light filter layer 310 is capable of blocking light within a specific wavelength range and filtering out noise light, and light within another specific wavelength range may pass through the light filter layer 310 and irradiate the pixel region 10 below.

Subsequently, a cap layer 320 is deposited on the light filter layer 310 and the liner layer 220, and the cap layer 320 may be a silicon nitride layer for example, but not limited thereto. According to the embodiment of the present invention, the cap layer 320 directly contacts the top surface of the light filter layer 310, and the light filter layer 310 is capped with the cap layer 320. According to the embodiment of the present invention, the cap layer 320, the liner layer 220 and the dielectric layer 204 may be used to completely block the metal ions in the light filter layer 310 from diffusing outward. A first passivation layer 330 is deposited on the cap layer 320 by a physical vapor deposition (PVD) process. The first passivation layer 330 may be metal oxide, such as tantalum oxide (TaO), but not limited thereto. A nanocavity construction layer 340, such as a silicon nitride layer, is then deposited on the first passivation layer 330, but not limited thereto.

Figure 6:
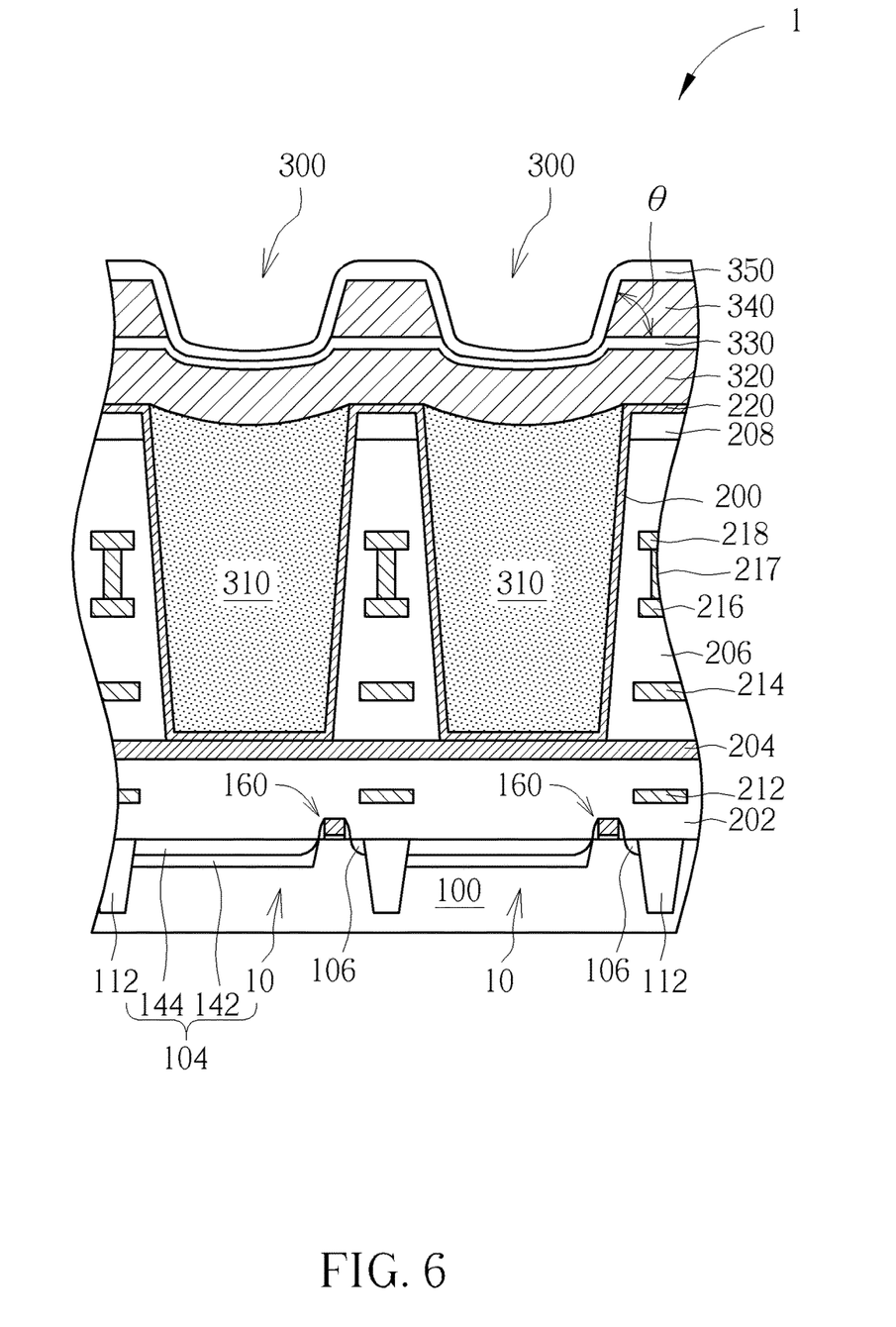

As shown in FIG. 6, a photolithographic process and an etching process are then performed for forming a nanocavity 300 in the nanocavity construction layer 340 directly above each of the light filer layers 310. A depth of the nanocavity 300 is substantially equal to a thickness of the nanocavity construction layer 340. The sidewall of the nanocavity 300 is a bevel sidewall, and an included angle θ between the sidewall and a horizontal level may range between 60 degrees and 80 degrees, but not limited thereto. Finally, a second passivation layer 350 is deposited conformally on the nanocavity construction layer 340, the sidewall of the nanocavity 300, and a bottom surface of the nanocavity 300 by a physical vapor deposition (PVD) process. The second passivation layer 350 may be metal oxide, such as tantalum oxide (TaO), but not limited thereto. The integrated bio-sensor with the nanocavity in the present invention may then be formed by the fabrication method described above.

Figure 7:
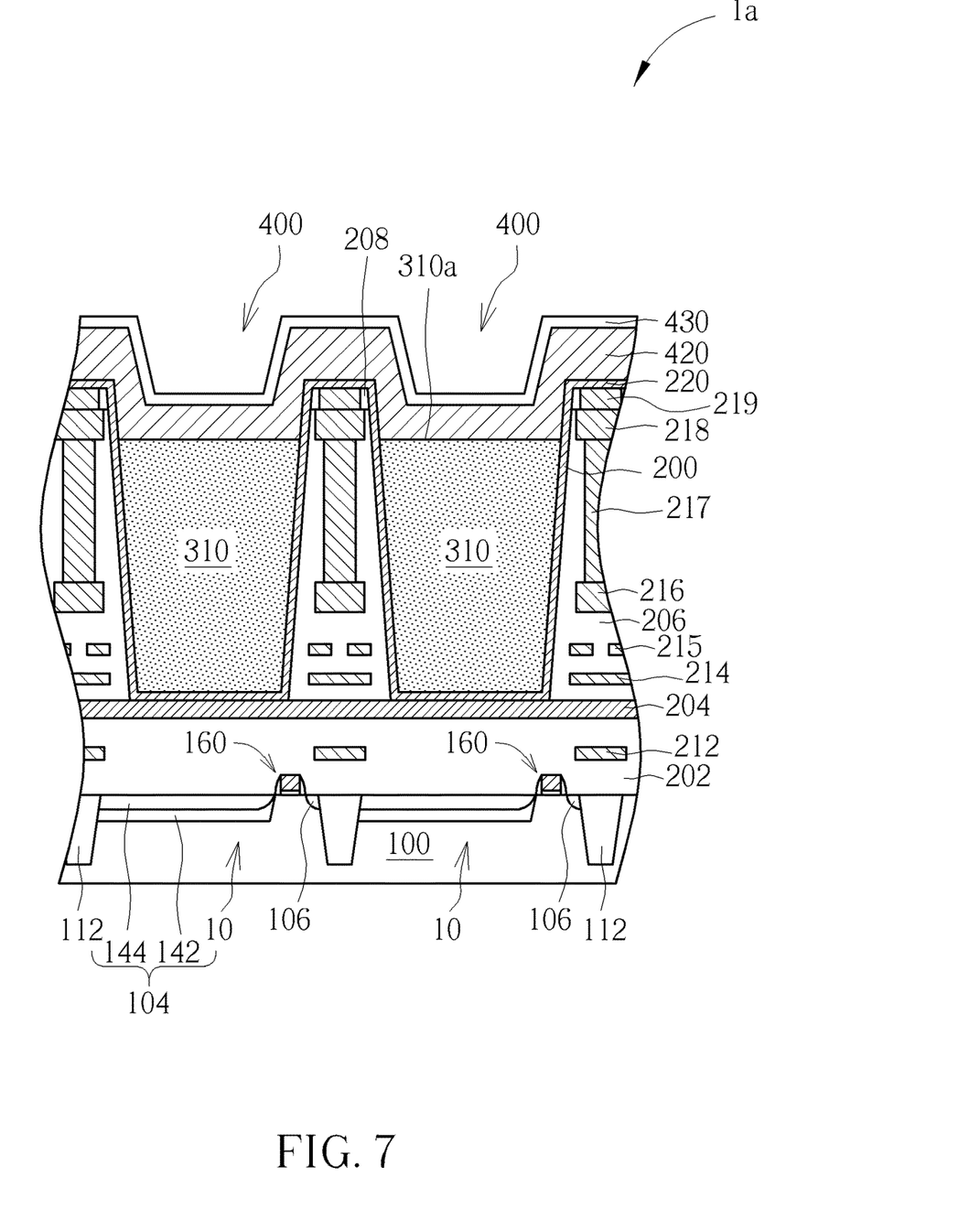
FIG. 7 is a schematic drawing illustrating a cross-sectional view of a bio-sensor with a self-aligned nanocavity according to another embodiment of the present invention.

Please refer to FIG. 7. FIG. 7 is a schematic drawing illustrating a cross-sectional view of a bio-sensor with a self-aligned nanocavity according to another embodiment of the present invention. As shown in FIG. 7, an integrated bio-sensor 1a also includes a substrate 100, and a plurality of pixel regions 10 arranged in an array configuration are formed in the substrate 100. For describing conveniently, there are only two pixel regions of the pixel array shown in the figure. According to the embodiment the present invention, the substrate 100 may be a silicon substrate, but not limited thereto. A plurality of isolation structures 112 are disposed on the substrate 100, and a plurality of the pixel regions 10 are defined by the isolation structures 112.

A gate structure 160 may be formed on the substrate 100 of each pixel region. A light-sensing region 104 and a floating drain region 106 are then formed in the substrate 100 at two sides of the gate structure 160. The gate structure 160 may include a dielectric layer and a conductive layer. The dielectric layer may be silicon oxide, and the conductive layer may be single-crystal silicon, undoped polycrystalline silicon, doped polycrystalline silicon, amorphous silicon, metal silicide, or the combination of the materials mentioned above. A sidewall spacer may be formed on the sidewall of the gate structure 160, and the sidewall spacer may be silicon oxide, silicon nitride, or the combination of silicon oxide and silicon nitride.

The light-sensing region 104 may be a photodiode including a first conductivity type doped region 142 and a second conductivity type doped region 144. The first conductivity type is an opposite conductivity type of the second conductivity type. For example, when the substrate is a P type substrate, the first conductivity type doped region 142 may be an N type doped region, the second conductivity type doped region 144 may be a P type doped region, the floating drain region 106 may be an N type doped region, and vice versa. For instance, the first conductivity type doped region 142 may be a lightly doped region, and the second conductivity type doped region 144 and the floating drain region 106 may be heavily doped regions.

According to the embodiment of the present invention, multiple dielectric layers, such as a dielectric layer 202, a dielectric layer 204, a dielectric layer 206, and a dielectric layer 208, may be formed on the substrate 100. For example, the dielectric layer 202 and the dielectric layer 206 may include silicon dioxide, but not limited thereto. The dielectric layer 204 disposed between the dielectric layer 202 and the dielectric layer 206 may include silicon nitride, but not limited thereto. According to the embodiment of the present invention, the dielectric layer 204 is used as a diffusion barrier layer. The dielectric layer 208 is used as a passivation layer or a protection layer, and the dielectric layer 208 may include silicon nitride, silicon oxynitride, and/or silicon oxide, but not limited thereto. According to the embodiment of the present invention, a metal layer 212 may be formed in the dielectric layer 202. A metal layer 214, a metal layer 216, a metal layer 218, and a metal connection 217 may be formed in the dielectric layer 206. It is noted that the metal layer structure in the dielectric layer shown in the figures is only used as an illustration sample.

According to the embodiment of the present invention, a trenched recess structure 200 is formed in the dielectric layer 206 and the dielectric layer 208 above the light-sensing region 104 corresponding to each pixel region 10. According to the embodiment of the present invention, a bottom part of the trenched recess structure 200 is a top surface of the dielectric layer 204. In other words, a depth of the trenched recess structure 200 is substantially equal to a total thickness of the dielectric layer 206 and the dielectric layer 208. According to the embodiment of the present invention, a liner layer 220, such as silicon nitride layer, is formed conformally on the bottom part and an inner wall of the trenched recess structure 200, but not limited thereto. According to the embodiment of the present invention, the liner layer 220 may be further formed on a top surface of the dielectric layer 208 for forming a continuous liner layer.

According to the embodiment of the present invention, the trenched recess structure 200 may be filled with at least one light filter layer 310. According to the embodiment of the present invention, the light filter layer 310 is capable of blocking light within a specific wavelength range (such as a green light laser) and filtering out noise light, and light within another specific wavelength range (such as a fluorescence generated by a specific biochemical reaction) may pass through the light filter layer 310 and irradiate the pixel region 10 below. Corresponding electrical current signals may be generated by the photoelectric reaction in the pixel region 10 and then be received by the light-sensing region 104.

According to the embodiment of the present invention, the light filter layer 310 may include high concentration metal ions, such as sodium ions. In order to prevent the metal ions from diffusing outward to the dielectric layer and inducing corrosion or deterioration of the metal layer, the surroundings and the bottom part of the light filter layer 310 are covered by the liner layer 220 for preventing the adjacent dielectric layer from directly contacting the light filter layer 310. Additionally, the dielectric layer 204 may be used as a diffusion barrier layer configured to keep the light filter layer 310 from diffusing downward to the surface of the substrate 100 and affecting the characteristics and performance of the devices.

According to the embodiment of the present invention, the light filter layer 310 has a top surface 310a, and the top surface 310a is lower than the top surface of the dielectric layer 208 by a predetermined depth for still forming a recess part at a top end of the trenched recess structure 200 after the step of forming the light filter layer 310. According to the embodiment of the present invention, a cap layer 420 is formed conformally on the light filter layer 310 and the liner layer 220, and the cap layer 420 may be a silicon nitride layer for example, but not limited thereto. According to the embodiment of the present invention, the cap layer 420 directly contacts the top surface of the light filter layer 310, and the light filter layer 310 is capped with the cap layer 420.

According to the embodiment of the present invention, a passivation layer 430 is formed conformally on the cap layer 420. The passivation layer 430 may be metal oxide, such as tantalum oxide, but not limited thereto. According to the embodiment of the present invention, the passivation layer 430 has to be transparent, acid resistant, and alkali-resistant. According to the embodiment of the present invention, the passivation layer 430 may be formed by a physical vapor deposition process, but not limited thereto. The cap layer 420 and the passivation layer 430 are self-aligned with the light filter layer 310 for forming a nanocavity 400 because the top surface 310a of the light filter layer 310 is lower than the top surface of the dielectric layer 208 by a predetermined depth for forming the recess part.

Additionally, according to the embodiment of the present invention, the metal layer 214, the metal layer 216, the metal layer 218, the metal connection 215, the metal connection 217, and a metal connection 219 may encompass the surroundings of the nanocavity 400 for reflecting the specific wavelength fluorescence generated by the biochemical reactions to the light-sensing region 104 and avoiding the interference of the light generated by the adjacent nanocavity 400.

Figure 8:
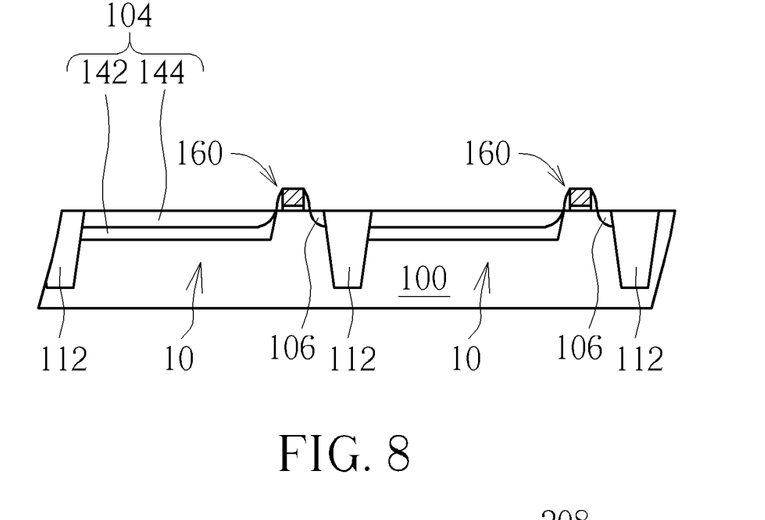
FIGS. 8-12 are schematic drawings illustrating a fabrication method of the bio-sensor with the self-aligned nanocavity in FIG. 7.

Please refer to FIGS. 8-12. FIGS. 8-12 are schematic drawings illustrating a fabrication method of the bio-sensor with the self-aligned nanocavity in FIG. 7. As shown in FIG. 8, a substrate 100 is also provided first. A plurality of pixel regions 10 arranged in an array configuration are formed in the substrate 100. For describing conveniently, there are only two pixel regions of the pixel array shown in the figures. According to the embodiment the present invention, the substrate 100 may be a silicon substrate, but not limited thereto. A plurality of isolation structures 112 are disposed on the substrate 100, and a plurality of the pixel regions 10 are defined by the isolation structures 112.

A gate structure 160 may be formed on the substrate 100 of each pixel region. A light-sensing region 104 and a floating drain region 106 are then formed in the substrate 100 at two sides of the gate structure 160. The gate structure 160 may include a dielectric layer and a conductive layer. The dielectric layer may be silicon oxide, and the conductive layer may be single-crystal silicon, undoped polycrystalline silicon, doped polycrystalline silicon, amorphous silicon, metal silicide, or the combination of the materials mentioned above. A sidewall spacer may be formed on the sidewall of the gate structure 160, and the sidewall spacer may be silicon oxide, silicon nitride, or the combination of silicon oxide and silicon nitride.

The light-sensing region 104 may be a photodiode including a first conductivity type doped region 142 and a second conductivity type doped region 144. The first conductivity type is an opposite conductivity type of the second conductivity type. For example, when the substrate is a P type substrate, the first conductivity type doped region 142 may be an N type doped region, the second conductivity type doped region 144 may be a P type doped region, the floating drain region 106 may be an N type doped region, and vice versa. For instance, the first conductivity type doped region 142 may be a lightly doped region, and the second conductivity type doped region 144 and the floating drain region 106 may be heavily doped regions.

Figure 9:
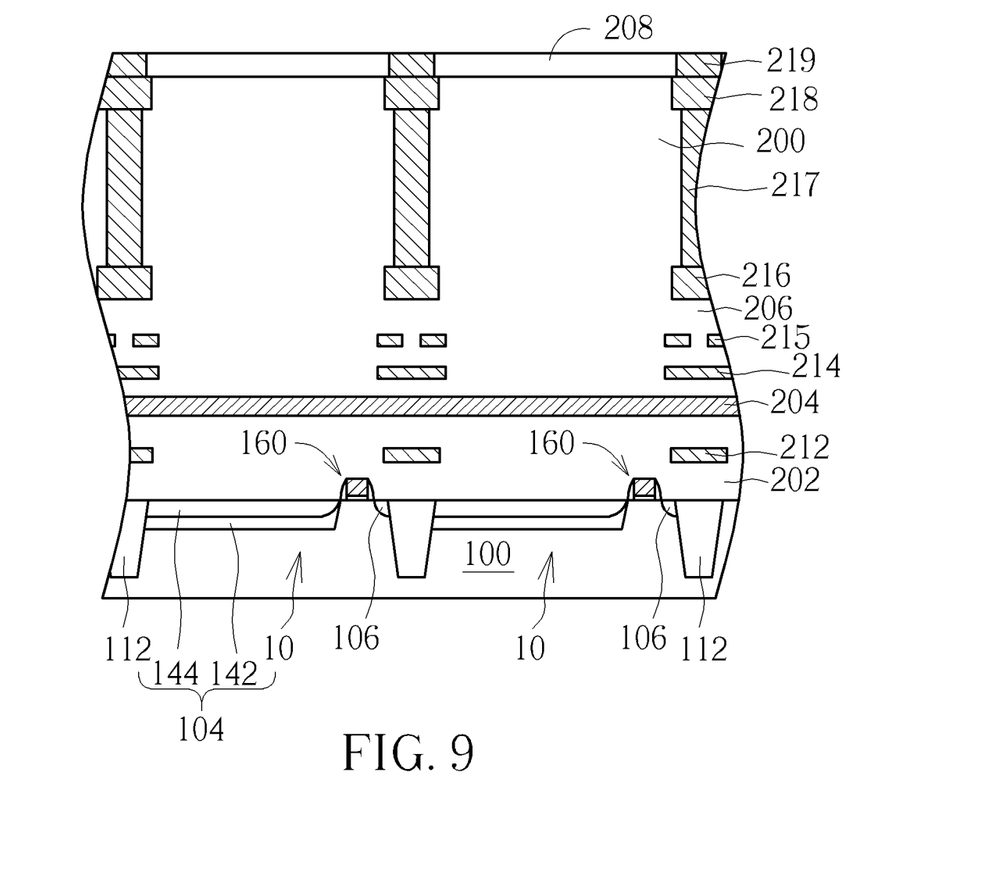

As shown in FIG. 9, multiple dielectric layers including a dielectric layer 202, a dielectric layer 204, a dielectric layer 206, and a dielectric layer 208, a metal layer 212, a metal layer 214, a metal layer 216, a metal layer 218, a metal connection 215, a metal connection 217, and a metal connection 219 are deposited on the substrate 100. For example, the dielectric layer 202 and the dielectric layer 206 may include silicon dioxide, but not limited thereto. The dielectric layer 202 and the dielectric layer 206 may be composed of multiple dielectric layers. The dielectric layer 204 formed between the dielectric layer 202 and the dielectric layer 206 may include silicon nitride, but not limited thereto. According to the embodiment of the present invention, the dielectric layer 204 is used as a diffusion barrier layer. The dielectric layer 208 is used as a passivation layer or a protection layer, and the dielectric layer 208 may include silicon nitride, silicon oxynitride, and/or silicon oxide, but not limited thereto. According to the embodiment of the present invention, the metal layer 212 may be formed in the dielectric layer 202. The metal layer 214, the metal layer 216, the metal layer 218, the metal connection 215, the metal connection 217, and the metal connection 219 may be formed in the dielectric layer 206 and the dielectric layer 208.

Figure 10:
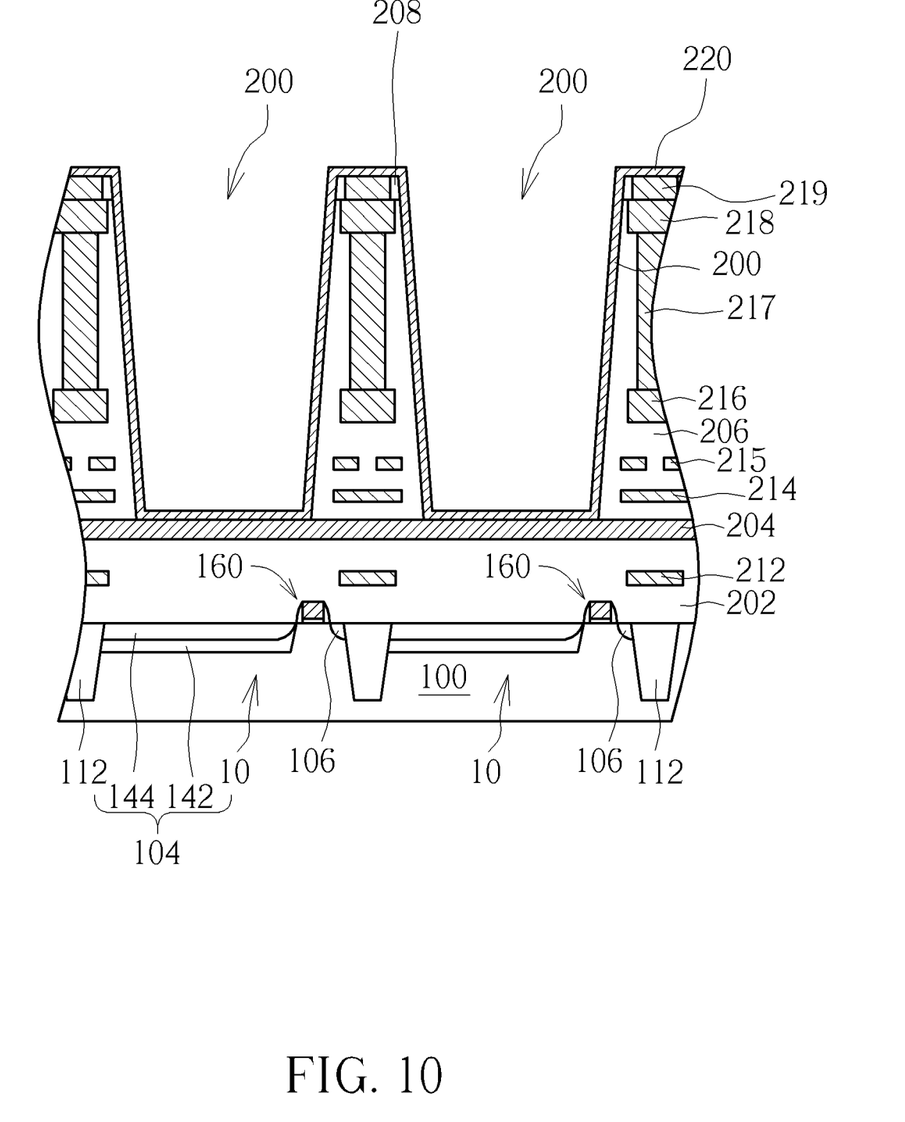

As shown in FIG. 10, a photolithographic process and an etching process are then performed to form a trenched recess structure 200 in the dielectric layer 206 and the dielectric layer 208 above the light-sensing region 104 corresponding to each pixel region 10. In the above-mentioned etching process for forming the trenched recess structure 200, the dielectric layer 204 may be used as an etching stop layer. According to the embodiment of the present invention, a bottom part of the trenched recess structure 200 is a top surface of the dielectric layer 204. In other words, a depth of the trenched recess structure 200 is substantially equal to a total thickness of the dielectric layer 206 and the dielectric layer 208. A liner layer 220, such as silicon nitride layer, is then deposited conformally on the bottom part and an inner wall of the trenched recess structure 200, but not limited thereto. According to the embodiment of the present invention, the liner layer 220 may be further formed on a top surface of the dielectric layer 208 for forming a continuous liner layer.

Figure 11:
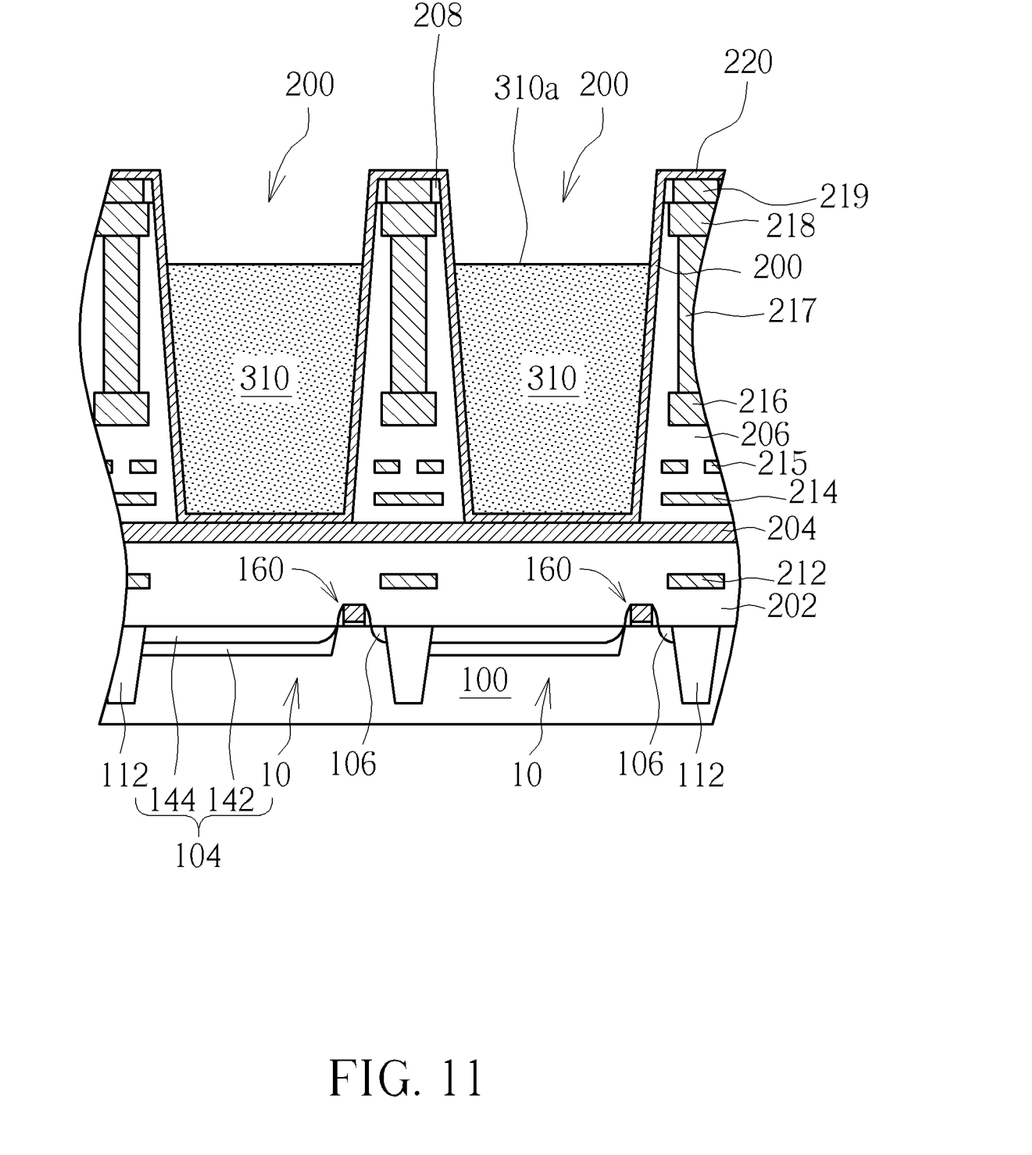

As shown in FIG. 11, the trenched recess structure 200 may then be filled with at least one light filter layer 310. According to the embodiment of the present invention, after the step of forming the light filter layer 310, a solidification process may then be performed for solidifying the light filter layer 310. According to the embodiment of the present invention, a polishing process may then be performed for removing the light filter layer 310 outside the trenched recess structure 200. An etching back process is then performed to make the top surface 310a lower than the top surface of the dielectric layer 208 by a predetermined depth for forming a recess part at a top end of the trenched recess structure 200. According to the embodiment of the present invention, the light filter layer 310 is capable of blocking light within a specific wavelength range and filtering out noise light, and light within another specific wavelength range may pass through the light filter layer 310 and irradiate the pixel region 10 below.

Figure 12:
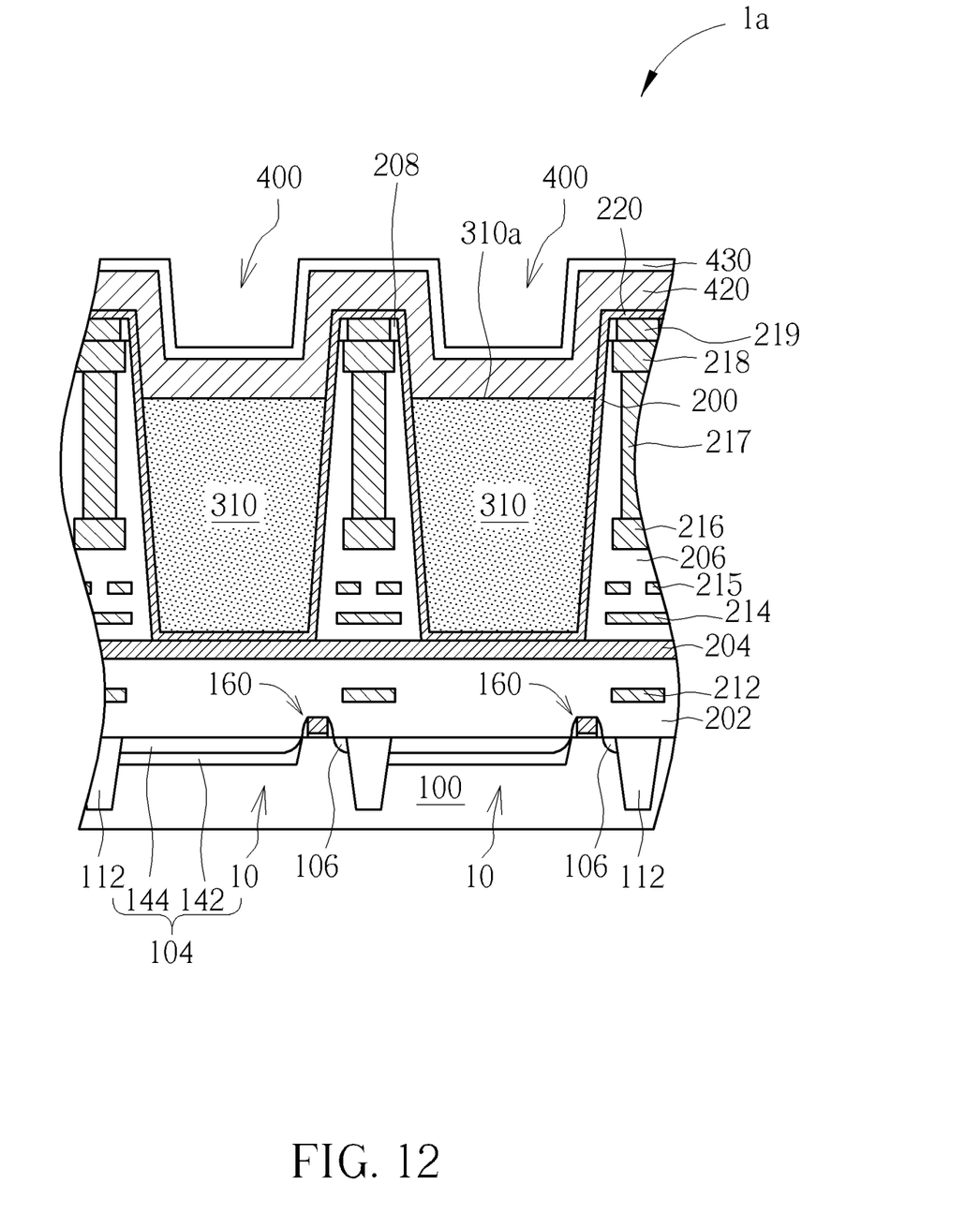

As shown in FIG. 12, subsequently, a cap layer 420 is formed conformally on the light filter layer 310 and the liner layer 220, and the cap layer 420 may be a silicon nitride layer for example, but not limited thereto. According to the embodiment of the present invention, the cap layer 420 directly contacts the top surface of the light filter layer 310, and the light filter layer 310 is capped with the cap layer 420. A passivation layer 430 is then formed conformally on the cap layer 420. The passivation layer 430 may be metal oxide, such as tantalum oxide, but not limited thereto. According to the embodiment of the present invention, the passivation layer 430 has to be transparent, acid resistant, and alkali-resistant. According to the embodiment of the present invention, the passivation layer 430 may be formed by a physical vapor deposition process, but not limited thereto. The cap layer 420 and the passivation layer 430 are self-aligned with the light filter layer 310 for forming a nanocavity 400 because of the recess part.

In the present invention, the integrated bio-sensor with the nanocavity is fabricated by the processes compatible with the manufacturing process of CMOS image sensor. The light filter layer 310 and the aligned nanocavity 300/400 may be directly formed above the light-sensing region 104 corresponding to each pixel region 10. The integrated bio-sensor in the present invention has the structure for acid and alkali resisting and anti-corrosion, and the metal ions in the light filter layer 310 may be kept from diffusing outward. The volume of each nanocavity 300/400 may be controlled precisely. Accordingly, the improved bio-sensor in the present invention has advantages such as fast, high accuracy, and high sensitivity, and the industrial utilization of the biosensor in the present invention is actually very high.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An integrated bio-sensor with a nanocavity, comprising:
   a substrate, wherein a plurality of isolation structures are disposed on the substrate, and a plurality of pixel regions are defined by the isolation structures;
   a light-sensing region disposed in each of the pixel regions;
   a first dielectric layer disposed on the substrate;
   a trenched recess structure disposed in the first dielectric layer and corresponding to the light-sensing region;
   a liner layer disposed conformally on an inner wall of the trenched recess structure;
   a light filter layer disposed on the liner layer in the trenched recess structure;
   a cap layer disposed on the trenched recess structure and directly contacting a top surface of the light filter layer;
   a first passivation layer disposed on the cap layer;
   a nanocavity construction layer disposed on the first passivation layer, wherein a nanocavity is disposed in the nanocavity construction layer disposed directly above the light filter layer; and
   a second passivation layer disposed on a sidewall and a bottom surface of the nanocavity.

2. The integrated bio-sensor with the nanocavity of claim 1, wherein the substrate comprises a silicon substrate.

3. The integrated bio-sensor with the nanocavity of claim 1, wherein the light-sensing region comprises a photodiode.

4. The integrated bio-sensor with the nanocavity of claim 1, further comprising a second dielectric layer disposed between the substrate and the first dielectric layer, wherein a bottom part of the trenched recess structure is a top surface of the second dielectric layer.

5. The integrated bio-sensor with the nanocavity of claim 1, wherein the light filter layer comprises metal ions.

6. The integrated bio-sensor with the nanocavity of claim 5, wherein the metal ions comprise a sodium ion.

7. The integrated bio-sensor with the nanocavity of claim 1, wherein the liner layer comprises a silicon nitride layer.

8. The integrated bio-sensor with the nanocavity of claim 1, wherein the first dielectric layer comprises a silicon oxide layer.

9. The integrated bio-sensor with the nanocavity of claim 4, wherein the second dielectric layer comprises a silicon nitride layer.

10. The integrated bio-sensor with the nanocavity of claim 1, wherein the first passivation layer and the second passivation layer comprise metal oxide.

11. The integrated bio-sensor with the nanocavity of claim 10, wherein the metal oxide comprises tantalum oxide.

12. The integrated bio-sensor with the nanocavity of claim 1, wherein a depth of the nanocavity is substantially equal to a thickness of the nanocavity construction layer.

13. The integrated bio-sensor with the nanocavity of claim 1, wherein the sidewall of the nanocavity is a bevel sidewall, and an included angle between the sidewall and a horizontal level ranges between 60 degrees and 80 degrees.

14. A fabrication method of an integrated bio-sensor with a nanocavity, comprising:
   providing a substrate, wherein a plurality of isolation structures are disposed on the substrate, and a plurality of pixel regions are defined by the isolation structures;
   forming a light-sensing region in each of the pixel regions;
   depositing a first dielectric layer on the substrate;
   forming a trenched recess structure in the first dielectric layer corresponding to the light-sensing region;
   forming a liner layer conformally on an inner wall of the trenched recess structure;
   forming a light filter layer on the liner layer, wherein the trenched recess structure is filled with the light filter layer;
   depositing a cap layer, wherein the cap layer directly contacts a top surface of the light filter layer;
   forming a first passivation layer on the cap layer;

depositing a nanocavity construction layer on the first passivation layer;

forming a nanocavity in the nanocavity construction layer directly above the light filter layer; and forming a second passivation layer on a sidewall and a bottom surface of the nanocavity.

15. The fabrication method of the integrated bio-sensor with the nanocavity of claim 14, wherein after the step of forming the light filter layer, the fabrication method further comprises:

performing a solidification process for solidifying the light filter layer; and performing a polishing process or an etching back process for removing the light filter layer outside the trenched recess structure.

16. The fabrication method of the integrated bio-sensor with the nanocavity of claim 14, wherein the first passivation layer and the second passivation layer are formed by physical vapor deposition processes.

17. The fabrication method of the integrated bio-sensor with the nanocavity of claim 14, wherein the substrate comprises a silicon substrate.

18. The fabrication method of the integrated bio-sensor with the nanocavity of claim 14, wherein the light-sensing region comprises a photodiode.

19. The fabrication method of the integrated bio-sensor with the nanocavity of claim 14, wherein the step of forming the trenched recess structure comprises:

forming a second dielectric layer and the first dielectric layer sequentially on the substrate; and performing an etching process to remove a part of the first dielectric layer, wherein the second dielectric layer is configured to be an etching stop layer in the etching process.

20. The fabrication method of the integrated bio-sensor with the nanocavity of claim 14, wherein the light filter layer comprises metal ions.

21. The fabrication method of the integrated bio-sensor with the nanocavity of claim 20, wherein the metal ions comprise a sodium ion.

22. The fabrication method of the integrated bio-sensor with the nanocavity of claim 14, wherein the liner layer comprises a silicon nitride layer.

23. The fabrication method of the integrated bio-sensor with the nanocavity of claim 14, wherein the first dielectric layer comprises a silicon oxide layer.

24. The fabrication method of the integrated bio-sensor with the nanocavity of claim 14, wherein the second dielectric layer comprises a silicon nitride layer.

25. The fabrication method of the integrated bio-sensor with the nanocavity of claim 14, wherein the first passivation layer and the second passivation layer comprise metal oxide.

26. The fabrication method of the integrated bio-sensor with the nanocavity of claim 25, wherein the metal oxide comprises tantalum oxide.

27. The fabrication method of the integrated bio-sensor with the nanocavity of claim 14, wherein a depth of the nanocavity is substantially equal to a thickness of the nanocavity construction layer.

28. The fabrication method of the integrated bio-sensor with the nanocavity of claim 14, wherein the sidewall of the nanocavity is a bevel sidewall, and an included angle between the sidewall and a horizontal level ranges between 60 degrees and 80 degrees.

* * * * *